United States Patent
Naing et al.

(10) Patent No.: US 11,951,266 B2
(45) Date of Patent: Apr. 9, 2024

(54) INTRAVENOUS CATHETER ASSEMBLY WITH CANNULA SAFETY MECHANISM

(71) Applicant: Becton, Dickinson and Company, Franklin Lakes, NJ (US)

(72) Inventors: Toe Toe Naing, Singapore (SG); Yun Hui Wong, Singapore (SG); Kiat Jin Cheng, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 237 days.

(21) Appl. No.: 17/083,094

(22) Filed: Oct. 28, 2020

(65) Prior Publication Data
US 2021/0038868 A1   Feb. 11, 2021

Related U.S. Application Data

(63) Continuation of application No. 15/872,529, filed on Jan. 16, 2018, now Pat. No. 10,850,070.

(30) Foreign Application Priority Data

Mar. 9, 2017  (SG) ........................... 10201701920Q

(51) Int. Cl.
*A61M 25/06*    (2006.01)
*A61M 5/158*   (2006.01)
(Continued)

(52) U.S. Cl.
CPC ........ *A61M 25/0637* (2013.01); *A61M 5/158* (2013.01); *A61M 25/0097* (2013.01);
(Continued)

(58) Field of Classification Search
CPC .......... A61M 25/0637; A61M 25/0097; A61M 25/0606; A61M 25/0631; A61M 25/0693;
(Continued)

(56) References Cited

U.S. PATENT DOCUMENTS 5,062,836 A   11/1991   Wendell
5,176,653 A    1/1993   Metais
(Continued)

FOREIGN PATENT DOCUMENTS

CN          1845768      10/2006
CN        103596616       2/2014
(Continued)

*Primary Examiner* — Dung T Ulsh
(74) *Attorney, Agent, or Firm* — Kirton McConkie; Whitney Blair; Kevin Stinger

(57) ABSTRACT

A catheter assembly may include a catheter adapter that includes a distal end, a proximal end, and an inner surface forming a lumen. The lumen may extend between the proximal end and the distal end. The catheter assembly may also include a cannula and a cannula hub. The cannula hub may include an outer portion disposed outside of the catheter adapter and an inner portion disposed within the catheter adapter. The cannula may extend distally from the inner portion. In response to the outer portion sliding proximally along an outer surface of the catheter adapter, the cannula may be withdrawn proximally into the catheter adapter. The outer portion may be configured to slide proximally to a locked position in which the cannula hub is locked with respect to the catheter adapter, and a distal tip of the cannula is disposed within the catheter adapter.

8 Claims, 3 Drawing Sheets

(51) Int. Cl.
*A61M 25/00* (2006.01)
*A61M 39/06* (2006.01)

(52) U.S. Cl.
CPC .... *A61M 25/0606* (2013.01); *A61M 25/0631* (2013.01); *A61M 2005/1583* (2013.01); *A61M 25/0693* (2013.01); *A61M 2039/066* (2013.01); *A61M 2205/273* (2013.01)

(58) Field of Classification Search
CPC .......... A61M 5/158; A61M 2005/1583; A61M 2039/066
See application file for complete search history.

(56) References Cited

U.S. PATENT DOCUMENTS

| | | | |
|---|---|---|---|
| 5,474,544 A | 12/1995 | Lynn | |
| 5,509,912 A | 4/1996 | Vaillancourt et al. | |
| 5,843,046 A | 12/1998 | Motisi et al. | |
| 6,206,851 B1 | 3/2001 | Prosl | |
| 10,850,070 B2 | 1/2020 | Naing et al. | |
| 2002/0177814 A1 | 11/2002 | Meng et al. | |
| 2006/0052755 A1 | 3/2006 | Lim et al. | |
| 2006/0184125 A1* | 8/2006 | Woehr | A61M 25/0618 604/164.07 |
| 2007/0093778 A1* | 4/2007 | Cindrich | A61M 5/158 604/500 |
| 2008/0287921 A1 | 11/2008 | Bennett | |
| 2009/0287154 A1 | 11/2009 | Harding et al. | |
| 2010/0222746 A1 | 9/2010 | Burkholz | |
| 2011/0160662 A1 | 6/2011 | Stout et al. | |
| 2013/0310751 A1 | 11/2013 | Davis et al. | |
| 2014/0039399 A1 | 2/2014 | Burkholz | |
| 2015/0148746 A1* | 5/2015 | Fujii | A61M 25/0631 604/164.08 |
| 2017/0043101 A1 | 2/2017 | Cole et al. | |
| 2018/0169388 A1* | 6/2018 | Hung | A61M 25/06 |

FOREIGN PATENT DOCUMENTS

| | | |
|---|---|---|
| CN | 102387831 B | 7/2014 |
| CN | 104334225 | 2/2015 |
| CN | 104540538 | 4/2015 |
| CN | 104740710 A | 7/2015 |
| DE | 202009009602 U1 | 12/2009 |
| EP | 0268480 A1 | 5/1988 |
| EP | 0875262 A2 | 11/1998 |
| EP | 1240916 A1 | 9/2002 |
| EP | 1399211 | 3/2004 |
| EP | 2578250 | 4/2013 |
| JP | H10258123 | 9/1998 |
| JP | 2004528127 | 9/2004 |
| JP | 2009513267 | 4/2009 |
| JP | 2013540486 | 11/2013 |
| JP | 2014528807 | 10/2014 |
| JP | 2017511224 A | 4/2017 |
| WO | 2002/096495 | 12/2002 |
| WO | 2008014436 A2 | 1/2008 |
| WO | 2013173311 A1 | 11/2013 |
| WO | 2016/179719 | 11/2016 |

\* cited by examiner

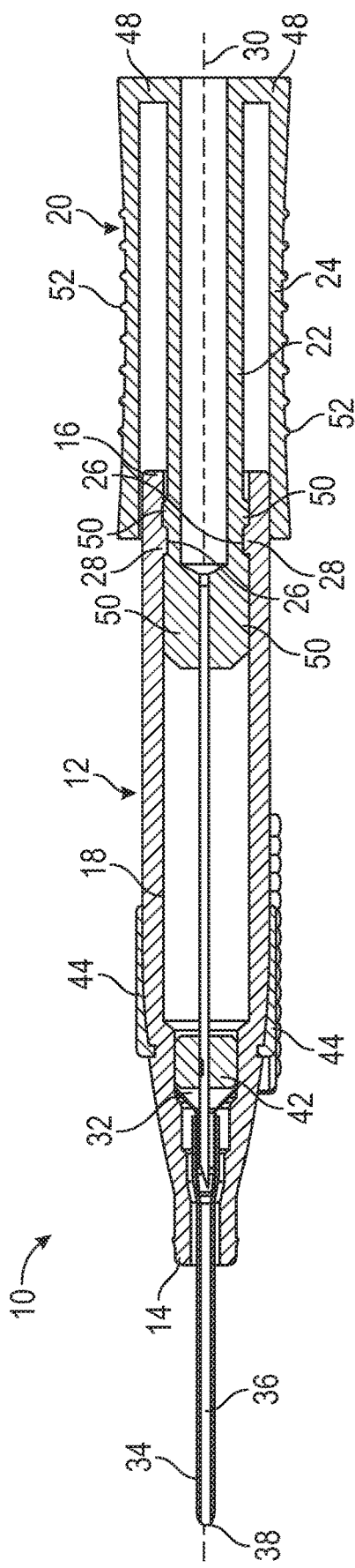
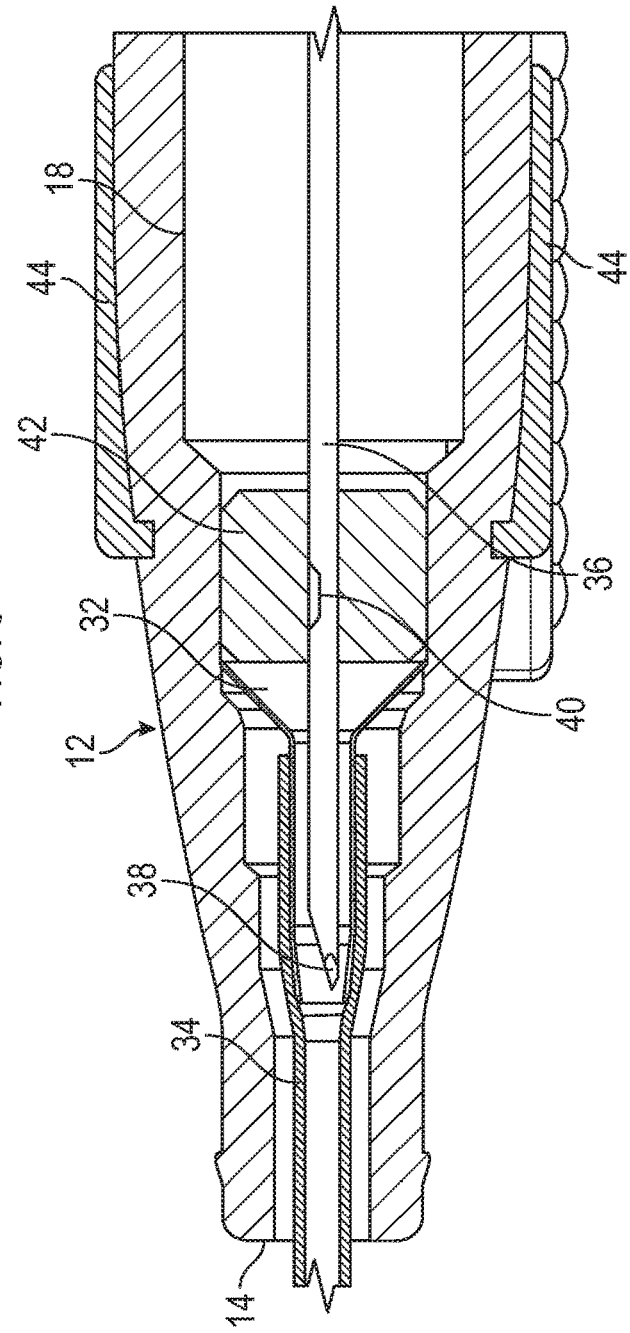
FIG. 3
FIG. 4

INTRAVENOUS CATHETER ASSEMBLY WITH CANNULA SAFETY MECHANISM

RELATED APPLICATIONS

This application is a continuation of U.S. patent application Ser. No. 15/872,529, filed Jan. 16, 2018, titled INTRAVENOUS CATHETER ASSEMBLY WITH CANNULA SAFETY MECHANISM, which claims priority to Singapore Application Number 10201701920Q, filed Mar. 9, 2017, titled INTRAVENOUS CATHETER ASSEMBLY WITH CANNULA SAFETY MECHANISM, which are incorporated herein in their entirety.

BACKGROUND OF THE INVENTION

Intravenous (IV) catheter assemblies are among the various types of vascular access devices. Over-the-needle peripheral IV catheters are a common IV catheter configuration. As its name implies, an over-the-needle catheter may be mounted over an introducer needle having a sharp distal tip. The introducer needle may be a hypodermic needle coupled to a needle assembly to help guide the needle and to facilitate its cooperation with the catheter. At least the inner surface of the distal portion of the catheter tightly may engage an outer surface of the introducer needle to prevent peelback of the catheter and, thereby, facilitate insertion of the catheter into the blood vessel. The catheter and the introducer needle may be assembled so that the distal tip of the introducer needle extends beyond the distal tip of the catheter. Moreover, the catheter and the introducer needle may be assembled so that, during insertion, the bevel of the introducer needle faces up, away from skin of a patient. The catheter and introducer needle may be inserted at a shallow angle through the skin into a blood vessel.

In order to verify proper placement of the introducer needle and/or catheter in the blood vessel, the user may confirm that there is "flashback" of blood into a flashback chamber associated with the needle assembly. Flashback generally entails the appearance of a small amount of blood, which is visible within the needle assembly or between the introducer needle and the catheter. Once proper placement of the distal tip of the catheter into the blood vessel is confirmed, the user may apply pressure to the blood vessel by pressing down on the skin over the blood vessel, distal to the introducer needle and the catheter. This finger pressure may momentarily occlude the vessel, reducing further blood flow through the introducer needle and the catheter.

The user may then withdraw the introducer needle from the catheter. The introducer needle may be withdrawn into a needle tip cover or needle cover that extends over the distal tip and prevents accidental needle sticks. In general, a needle tip cover may include a casing, sleeve, or other similar device that is designed to trap or capture the distal tip when the introducer needle is withdrawn from the catheter and the patient. After the introducer needle is withdrawn, the catheter may be left in place to provide intravenous access to the patient.

The separation of the introducer needle assembly from catheter portions of the catheter assembly presents numerous potential hazards to the users and others in the area. As indicated above, there is a risk of accidental needle sticks if the distal tip is not secured properly. Additionally, because the introducer needle has been in contact with blood in vasculature of the patient, blood may be present on an exterior of the introducer needle as well as inside a lumen of the introducer needle. As the introducer needle is withdrawn from the catheter, there is a risk that the blood will drip from the distal tip or come into contact with other surfaces to expose people and equipment to blood.

Additionally, it has been observed that withdrawing the introducer needle from a catheter assembly may impart energy to parts of the needle assembly. For instance, during withdrawal of the introducer, bending forces can be applied (either unintentionally or intentionally) to the introducer needle. The bending forces on the introducer needle may cause blood to splatter or spray from the introducer needle when the needle vibrates and shakes as it becomes free from the catheter assembly and releases stored energy. Accordingly, there is a need in the art for devices, systems, and methods that provide catheter assemblies with increased needle safety.

BRIEF SUMMARY OF THE INVENTION

The present disclosure relates generally to an intravenous catheter assembly and associated devices, systems, and methods. In some embodiments, the catheter assembly may be used for infusion and/or blood collection. In some embodiments, the catheter assembly may include a catheter adapter, which may include a distal end, a proximal end, and an inner surface forming a lumen. In some embodiments, the lumen may extend between the proximal end and the distal end of the catheter adapter.

In some embodiments, the catheter assembly may include a cannula hub, which may be configured to slide with respect to the catheter adapter from a distal, unlocked position to a proximal, locked position. In some embodiments, the cannula hub may include an inner portion and/or an outer portion. In some embodiments, the outer portion may at least partially surround the inner portion. In some embodiments, the inner portion may be disposed within the lumen of the catheter adapter.

In some embodiments, the inner portion may include a first interlock portion, and an inner surface of the catheter adapter may include a second interlock portion. In some embodiments, when the cannula hub is in the locked position, the first interlock portion and the second interlock portion may interlock or be coupled together, which may prevent movement of the cannula hub with respect to the catheter adapter. In some embodiments, when the cannula hub is in the unlocked position, the first interlock portion and the second interlock portion may be uncoupled, which may allow movement of the cannula hub with respect to the catheter adapter in a direction aligned with a longitudinal axis of the catheter adapter.

In some embodiments, the first interlock portion may include a receiving portion and the second interlock portion may include an engaging portion. Alternatively, in some embodiments, the first interlock portion may include the engaging portion and the second interlock portion may include the receiving portion. In some embodiments, the receiving portion may include one or more grooves, and the engaging portion may include one or more corresponding protrusions. In some embodiments, the engaging portion and the receiving portion may interlock or be coupled together when the cannula hub is in the locked position. In some embodiments, the cannula may be entirely disposed within the catheter adapter when the cannula hub is in the locked position.

In some embodiments, the catheter assembly may include a cannula, which may include a distal tip. In some embodiments, the cannula may include an elongated tubular shaft and an inner lumen formed by the elongated tubular shaft. In some embodiments, the tubular shaft may include a notch, which may improve first stick success and allow observation of blood flashback. In some embodiments, the cannula may extend distally from the cannula hub. In further detail, in some embodiments, the cannula may extend distally from the inner portion of the cannula hub.

In some embodiments, the outer portion of the cannula hub may be generally cylindrical and/or disposed outside of the catheter adapter. In some embodiments, the outer portion may be configured to slide proximally along an outer surface of the catheter adapter until the cannula hub reaches the locked position. In some embodiments, in response to the outer portion of the cannula hub sliding proximally along the outer surface of the catheter adapter, the cannula may be withdrawn proximally into the catheter adapter. In some embodiments, the outer portion of the cannula hub may be configured to slide proximally to the locked position in which the cannula hub may be locked with respect to the catheter adapter, preventing removal of the cannula from the catheter assembly, reducing a risk of needle stick injury, and discouraging reuse of the catheter assembly. In some embodiments, when the cannula hub is in the locked position, the distal tip may be disposed within the catheter adapter, also reducing the risk of needle stick injury. In some embodiments, the outer portion of the cannula hub may include a grip, which may be configured to be gripped by a user when the catheter assembly is inserted into a blood vessel of a patient. In some embodiments, the cannula hub may be slid to the locked position as the user grips the grip and slides the outer portion of the cannula hub to the locked position.

In some embodiments, the catheter assembly may include a wedge, which may be funnel-shaped. In some embodiments, the wedge may be constructed of metal. In some embodiments, a catheter tube of the catheter assembly may be connected to the wedge. In some embodiments, the wedge may be configured to couple the catheter tube to the catheter adapter. In some embodiments, the wedge may be disposed in a distal portion of the lumen. In some embodiments, the wedge may be frictionally wedged into the distal portion of the lumen. In some embodiments, when the cannula hub is in the locked position, the distal tip of the cannula may be disposed within the wedge, which may prevent skiving of the catheter tube by the distal tip.

In some embodiments, the catheter assembly may include a septum, which may be disposed within the lumen of the catheter adapter. In some embodiments, the septum may be proximate and/or proximal to the wedge. In some embodiments, when the cannula is withdrawn and the cannula hub is in the locked position, the notch may be disposed within the septum, which may prevent fluid from leaking out of the notch and/or into the lumen of the catheter adapter.

In some embodiments, the catheter assembly may include a safety winged blood collection set. In these and other embodiments, the catheter assembly may include a winged element, which may be coupled to the catheter adapter. In some embodiments, the winged element may include one or more wings, which may extend outwardly from the catheter adapter and may be secured to skin of a patient. In some embodiments, when the cannula hub is in the unlocked position, a distal end of the cannula hub may be disposed proximate or abutting the winged element. In some embodiments, the winged element may act as a stop for the cannula hub, contacting the cannula hub and preventing the cannula hub from sliding beyond the winged element. In some embodiments, the catheter tube may improve comfort of a patient when the catheter assembly having the winged element is inserted into the blood vessel of the patient.

BRIEF DESCRIPTION OF THE SEVERAL VIEWS OF THE FIGURES

In order that the manner in which the above-recited and other features and advantages of the invention will be readily understood, a more particular description of the catheter assembly with cannula safety mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which:

FIG. 3 is an upper perspective view of the catheter assembly of FIG. 1, illustrating the cannula hub in a locked position, according to some embodiments;

FIG. 4 is a cross-sectional view of the catheter assembly of FIG. 1, illustrating the cannula hub in the locked position, according to some embodiments.

DETAILED DESCRIPTION OF THE INVENTION

The presently preferred embodiments of the described invention will be best understood by reference to FIGS. 1-5, wherein like parts are designated by like numerals throughout. It will be readily understood that the components of the present invention, as generally described and illustrated in FIGS. 1-5 in the present disclosure, could be arranged and designed in a wide variety of different configurations. Thus, the following more detailed description of the embodiments of the catheter assembly, and associated devices, systems, and methods, is not intended to limit the scope of the invention, as claimed, but is merely representative of some embodiments of the invention.

Figure 1:
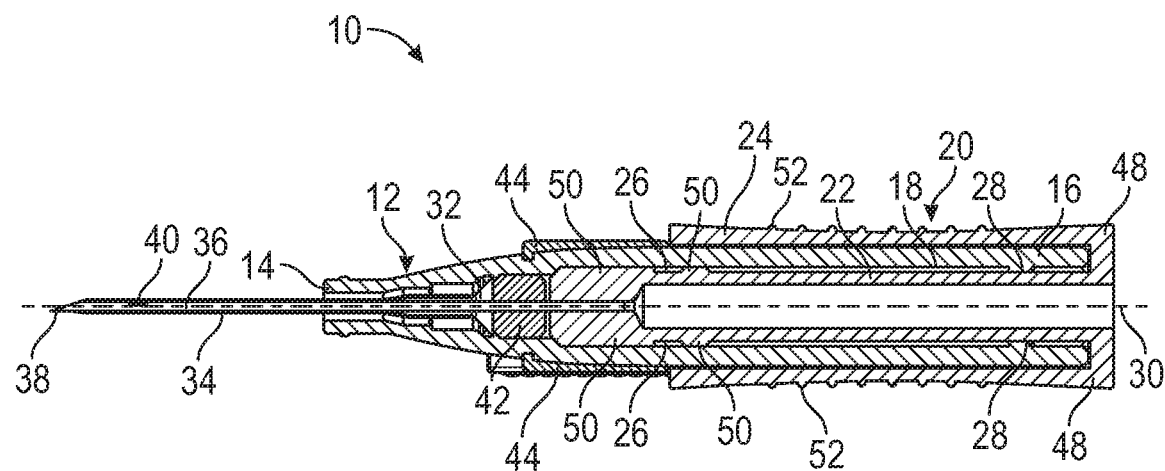
FIG. 1 is an upper perspective view of an example catheter assembly, illustrating a cannula hub in an unlocked position, according to some embodiments.
Figure 2:
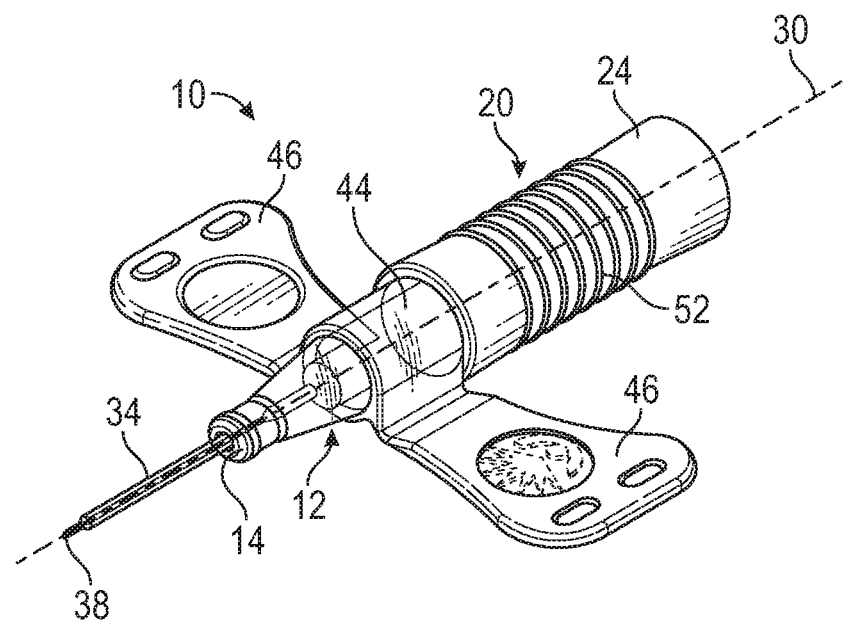
FIG. 2 is a cross-sectional view of the catheter assembly of FIG. 1, illustrating the cannula hub in the unlocked position, according to some embodiments.

The present disclosure relates generally to a catheter assembly and associated devices, systems, and methods. Referring now to FIGS. 1-2, in some embodiments, the catheter assembly 10 may include a catheter adapter 12, which may include a distal end 14, a proximal end 16, and an inner surface 18 forming a lumen. In some embodiments, the lumen may extend between the proximal end 16 and the distal end 18 of the catheter adapter 12.

Figure 5:
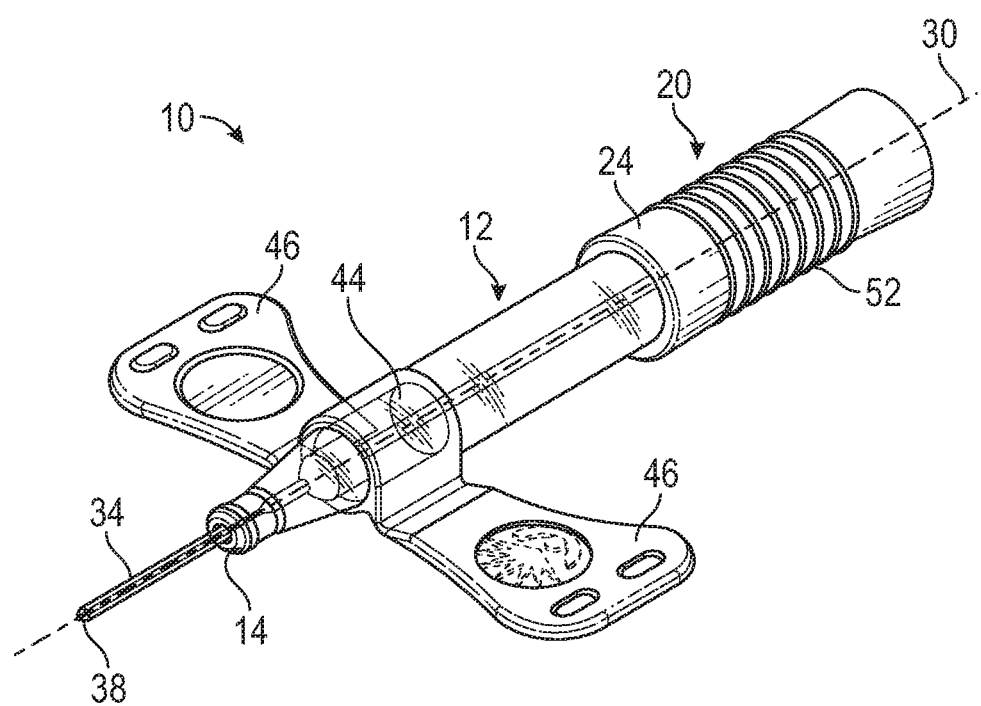
FIG. 5 is an enlarged cross-sectional view of a portion of the catheter assembly of FIG. 1, illustrating the cannula hub in the locked position, according to some embodiments.

In some embodiments, the catheter assembly 10 may include a cannula hub 20, which may be configured to slide with respect to the catheter adapter 12 from a distal, unlocked position, illustrated in FIGS. 1-2, to a proximal, locked position, illustrated in FIGS. 3-5. In some embodiments, the cannula hub 20 may include an inner portion 22 and/or an outer portion 24. In some embodiments, the inner portion 22 may be at least partially disposed within the lumen of the catheter adapter 12.

In some embodiments, the inner portion 22 of the cannula hub 20 may include a first interlock portion, and the inner surface 18 of the catheter adapter 12 may include a second interlock portion. In some embodiments, when the cannula hub 20 is in the unlocked position, the first interlock portion and the second interlock portion may be uncoupled, which may allow movement of the cannula hub 20 with respect to the catheter adapter 12 in a direction aligned with a longitudinal axis 30 of the catheter adapter 12. In some embodiments, the first interlock portion may include one or more grooves 26, and the second interlock portion may include one or more corresponding protrusions 28. Additionally or alternatively, in some embodiments, the first interlock portion may include one or more protrusions 28 and the second interlock portion may include one or more grooves 26.

In some embodiments, the catheter assembly 10 may include a wedge 32, which may be funnel-shaped. In some embodiments, a catheter tube 34 of the catheter assembly 10 may be coupled with the wedge 32. For example, a neck portion of the wedge 32 may be inserted into a proximal end of the catheter tube 34 in a friction or interference fit. In some embodiments, the wedge 32 and the catheter tube 34 may be integrally formed. In some embodiments, the wedge 32 may be configured to couple the catheter tube 34 to the catheter adapter 12. In some embodiments, the wedge 32 may be frictionally wedged into a distal portion of the lumen.

In some embodiments, the catheter assembly 10 may include a cannula 36, which may be an introducer needle. In some embodiments, the cannula 36 may include a sharp distal tip 38. In some embodiments, the wedge 32 may be constructed of metal, plastic, or another rigid material to prevent skiving of the catheter tube 34 by the distal tip 38. In some embodiments, the cannula 36 may include an elongated tubular shaft and an inner lumen formed by the elongated tubular shaft. In some embodiments, the tubular shaft may include a notch 40, which may improve first stick success. In some embodiments, the cannula 36 may extend distally from the cannula hub 20. In further detail, in some embodiments, the cannula 36 may be coupled to and extend distally from the inner portion 22 of the cannula hub 20. In some embodiments, a fluid pathway of the catheter assembly 10 may extend through the inner portion 22 of the cannula hub 20 and the cannula 36. In some embodiments, the inner portion 22 may be coupled with tubing (not illustrated), which may be part of the fluid pathway.

In some embodiments, the catheter assembly 10 may include a septum 42, which may be disposed within the lumen of the catheter adapter 12. In some embodiments, the septum 42 may be proximal to the wedge 32. In some embodiments, the septum 42 may be proximate to and contacting the wedge 32, which may facilitate alignment with the notch 40 when the cannula hub 20 is in the locked position. In some embodiments, the septum 42 may include one or more slits that may be pre-cut, or the septum 42 may be slit-less. In some embodiments, the septum 42 may be constructed of a resilient material. In some embodiments, the septum 42 may be constructed of silicon and/or polytetrafluoroethylene.

In some embodiments, the catheter assembly 10 may include a winged element 44, which may be coupled to the catheter adapter 12. In some embodiments, the winged element 44 may extend around an exterior of the catheter adapter 12. In some embodiments, the winged element 44 may include one or more wings 46, which may extend outwardly from the catheter adapter 12. In some embodiments, when the cannula hub 20 is in the unlocked position, a distal end of the cannula hub 20 may be disposed proximate the winged element 44. In some embodiments, the winged element 44 may act as a stop for the cannula hub 20, contacting the cannula hub 20 and preventing the cannula hub 20 from sliding distally beyond the winged element 44. Additionally or alternatively, in some embodiments, one or more junctions 48 between the inner portion 22 and outer portion 24 may limit distal movement of the cannula hub 20. In some embodiments, the catheter tube 34 may improve comfort of a patient when the catheter assembly 10 having the winged element 44 is inserted into the blood vessel of the patient.

Referring now to FIGS. 3-5, in some embodiments, when the cannula hub 20 is in the locked position, the first interlock portion and the second interlock portion may interlock or be coupled together, which may prevent movement of the cannula hub 20 with respect to the catheter adapter 12. In some embodiments, the first interlock portion may include a receiving portion and the second interlock portion may include an engaging portion. Alternatively, in some embodiments, the first interlock portion may include the engaging portion and the second interlock portion may include the receiving portion. In some embodiments, the receiving portion may include one or more grooves 26, and the engaging portion may include one or more protrusions 28 corresponding to the grooves 26. In some embodiments, the engaging portion and the receiving portion may interlock or be coupled together when the cannula hub 20 is in the locked position. In some embodiments, the cannula 36 may be entirely disposed within the catheter adapter 12 when the cannula hub 20 is in the locked position.

In some embodiments, when the cannula hub 20 is in the locked position, illustrated in FIGS. 3-5, the distal tip 38 of the cannula 36 may be disposed within the wedge 32, which may prevent skiving of the catheter tube 34 by the distal tip 38. In some embodiments, when the cannula 36 is withdrawn proximally into the catheter adapter 12 such that the cannula hub 20 is in the locked position, the notch 40 may be disposed within the septum 42, which may prevent fluid from leaking out of the notch 40 and/or into the lumen of the catheter adapter 12. In some embodiments, the notch 40 may be in fluid communication with the fluid pathway such that fluid travelling through the fluid pathway may exit the cannula 36 through the notch 40 if the notch is not sealed or blocked by the septum 42.

In some embodiments, a particular groove 26 may be configured to engage a particular protrusion 28 in the locked position. For example, the particular groove 26 may engage the particular protrusion 28 in a snap or interference fit. As illustrated in FIGS. 1 and 3, in some embodiments, the particular groove 26 may be formed between two protrusions 50 of the inner portion 22 of the cannula hub 20, which may extend outwardly from an outer surface of the inner portion 22. In some embodiments, the two protrusions 50 may contact the inner surface 18 of the catheter adapter 12, which may support the inner portion 22 within the lumen. In some embodiments, the particular protrusion 28 may contact the outer surface of the inner portion 22, which may support the inner portion 22 within the lumen. In some embodiments, an inner surface of the outer portion 24 may include the first interlock portion, and an outer surface of the catheter adapter 12 may include the second interlock portion.

In some embodiments, the outer portion 24 may at least partially surround the inner portion 22. In some embodiments, the inner portion 22 may be at least partially disposed within the lumen of the catheter adapter 12. In some embodiments, the outer portion 24 of the cannula hub 20 may be generally cylindrical and/or disposed outside of the catheter adapter 12.

In some embodiments, the outer portion 24 may be configured to slide proximally along an outer surface of the catheter adapter 12 until the cannula hub 20 reaches the locked position. In some embodiments, in response to the outer portion 24 of the cannula hub 20 sliding proximally along the outer surface of the catheter adapter 12, the cannula 36 may be withdrawn proximally into the catheter adapter 12. In some embodiments, the outer portion 24 of the cannula hub 20 may be configured to slide proximally to the locked position in which the cannula hub 20 may be locked with respect to the catheter adapter 12, preventing removal of the cannula 36 from the catheter assembly 12, reducing a risk of needle stick injury, and discouraging reuse of the catheter assembly 12. In some embodiments, when the cannula hub 20 is in the locked position, the distal tip 38 may be disposed within the catheter adapter 12, also reducing the risk of needle stick injury. In some embodiments, the outer portion 24 of the cannula hub 20 may include a grip 52, which may be configured to be gripped by a user when the catheter assembly 12 is inserted into a blood vessel of a patient. In some embodiments, the grip 52 may include one or more ribs or other protrusions to facilitate gripping.

In some embodiments, the cannula hub 20 may be slid to the locked position as the user grips the grip and slides the outer portion 24 of the cannula hub 20 to the locked position. In some embodiments, the locked position may be passively activated. In further detail, in some embodiments, the cannula hub 20 may slide to the locked position in a passive manner, requiring no additional steps other than those normally used in catheter introduction. In some embodiments, when the cannula hub 20 is in between the unlocked position and the locked position, the cannula hub 20 may freely move proximally or distally along the catheter adapter 12, which may allow adjustment of the distal tip 38 such as, for example, during hooding of the cannula 36.

The present invention may be embodied in other specific forms without departing from its structures, methods, or other essential characteristics as broadly described herein and claimed hereinafter. For example, it is understood that the catheter assembly 10 may include any number of interlock portions, which may include any variety of mechanisms capable of preventing movement between the catheter adapter 12 and the cannula hub 20. As another example, the cannula hub 20 may include one or more adapters or connectors and/or may be coupled to tubing, which may allow another device to be connected to the catheter assembly 10. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A catheter assembly, comprising:
   a catheter adapter comprising a distal end, a proximal end, and an inner surface forming a lumen, wherein the lumen extends between the proximal end and the distal end;
   a catheter tube extending distally from the catheter adapter;
   a cannula hub configured to slide with respect to the catheter adapter from a distal, unlocked position to a proximal, locked position;
   a cannula comprising a sharp distal tip and a notch, wherein the cannula extends distally from the cannula hub and wherein a position of the cannula is secured relative to the catheter adapter when the cannula hub is in the locked position; and
   a septum disposed within the lumen, wherein the notch is secured within the septum when the cannula hub is in the locked position, thereby preventing fluid from leaking out of the notch into the lumen, wherein the sharp distal tip of the cannula is disposed distal to the septum and within the catheter adapter when the cannula hub is in the locked position; and
   a winged element coupled with the catheter adapter and comprising one or more wings, wherein the cannula hub comprises an outer portion disposed outside of the catheter adapter and configured to slide proximally along an outer surface of the catheter adapter towards the proximal end of the catheter adapter monolithically formed as a single unit with the distal end of the catheter adapter until the cannula hub reaches the locked position, wherein the winged element is configured to contact a distal end of the outer portion to act as a stop for the cannula hub and prevent the cannula hub from sliding distally beyond the winged element.

2. The catheter assembly of claim 1, further comprising a wedge disposed within the catheter adapter and configured to couple the catheter tube to the catheter adapter.

3. The catheter assembly of claim 2, wherein the wedge is funnel-shaped.

4. The catheter assembly of claim 1, wherein when the cannula hub is in the unlocked position, a distal end of the outer portion is disposed proximate the winged element.

5. The catheter assembly of claim 1, wherein the cannula hub comprises an inner portion disposed within the lumen, wherein the inner portion comprises a first interlock portion and the inner surface of the catheter adapter comprises a second interlock portion, wherein the second interlock portion is monolithically formed as a single unit with the distal end of the catheter adapter, wherein the first interlock portion and the second interlock portion are configured to interlock when the cannula hub is in the locked position to prevent movement of the cannula hub with respect to the catheter adapter.

6. The catheter assembly of claim 1, wherein the outer portion is generally cylindrical.

7. The catheter assembly of claim 2, wherein the wedge is constructed of metal.

8. A catheter assembly, comprising:
   a catheter adapter comprising a distal end, a proximal end, and an inner surface forming a lumen, wherein the lumen extends between the proximal end and the distal end;
   a catheter tube extending distally from the catheter adapter;
   a cannula hub configured to slide with respect to the catheter adapter from a distal, unlocked position to a proximal, locked position;
   a cannula comprising a sharp distal tip and a notch, wherein the cannula extends distally from the cannula hub and wherein a position of the cannula is secured relative to the catheter adapter when the cannula hub is in the locked position; and
   a septum disposed within the lumen, wherein the notch is secured within the septum when the cannula hub is in the locked position, thereby preventing fluid from leaking out of the notch into the lumen, wherein the sharp distal tip of the cannula is disposed distal to the septum and within the catheter adapter when the cannula hub is in the locked position, wherein the cannula hub comprises an outer portion disposed outside of the catheter adapter and configured to slide proximally along an outer surface of the catheter adapter towards the proximal end of the catheter adapter monolithically formed as a single unit with the distal end of the catheter adapter until the cannula hub reaches the locked position.

\* \* \* \* \*